United States Patent [19]

Howard et al.

[11] Patent Number: 5,264,569
[45] Date of Patent: Nov. 23, 1993

[54] PURIFIED FUNGAL SPORE TIP MUCILAGE

[75] Inventors: Richard J. Howard, Wilmington, Del.; James A. Sweigard, Elkton, Md.; William D. Hitz, Wilmington, Del.; Forrest G. Chumley, Wilmington, Del.; Barbara S. Valent, Wilmington, Del.

[73] Assignee: E. I. Du Pont de Nemours and Company, Wilmington, Del.

[21] Appl. No.: 842,661

[22] Filed: Feb. 27, 1992

Related U.S. Application Data

[63] Continuation-in-part of Ser. No. 536,918, Jun. 12, 1990, abandoned.

[51] Int. Cl.$^5$ .............................................. C08B 37/00
[52] U.S. Cl. .................................... 536/114; 435/101; 536/128
[58] Field of Search ............... 435/101; 536/114, 128

[56] References Cited

U.S. PATENT DOCUMENTS 4,496,397  1/1985  Waite .................. 106/161
4,585,585  4/1986  Waite .................. 260/112.5 R

FOREIGN PATENT DOCUMENTS 242656  10/1987  European Pat. Off. .

OTHER PUBLICATIONS

Babczinski, Z. Naturforsch, 390, 222–231, 1984.
Williams, Mycologia, 75, 215–256, 1983.
Gubler et al., Protoplasma, 149, 24–30, 1989.
Horn, Mycologia, 81, 742–753, 1989.
Blackwell, Mycologia, 81, 735–741, 1989.
Sangar et al., Chemical Abstracts, vol. 79(13), #7 5645d.
Babczinski, Chemical Abstracts, vol. 101(1), #2437a.
Williams, Chemical Abstracts, vol. 77, #14814.
Hamer et al., Science 239:288, 1988.
Williams, Biological Abstracts vol. 77(2), 1984, #14814.

Primary Examiner—Ronald W. Griffin
Assistant Examiner—Pamela S. Webber

[57] ABSTRACT

A purified fungal spore tip mucilage isolated from the conidia of Magnaporthe grisea and the process of isolation thereof.

5 Claims, No Drawings

PURIFIED FUNGAL SPORE TIP MUCILAGE

CROSS-REFERENCE TO RELATED APPLICATION

This application is a continuation-in-part of copending application U.S. Ser. No. 07/536,918 filed Jun. 12, 1990, now abandoned.

BACKGROUND OF THE INVENTION

The present invention relates to novel adhesive mucilage isolated from the fungus *Mggnaporthe grisea*, and to procedures for such isolation.

Many biological organisms must attach to a surface for survival. This attachment often occurs in an aqueous habitat. This is an interesting phenomenon since adhesion in aqueous environments is difficult because adhesives are generally adversely affected by the presence of water on the substrates being adhered. Water competes with the adhesive for the surface, tends to hydrolyze the adhesive, and frequently plasticizes it. Accordingly, it is usually required that the substrate surfaces being adhered be substantially free from water or other aqueous impurities. As can be appreciated, such conditions are not always possible, particularly for bioadhesives used in medical and dental applications and employing a wide variety of substrates such as those encountered when gluing or restoring fractured hard tissue in the body such as bone, cartilage and teeth, as well as ligaments, blood vessels and the like.

It would be useful if natural bioadhesives could be routinely isolated and adapted for industrial applications. Unfortunately, this is not the case. Attempts to isolate them generally would be expected to be attended by significant difficulties due to the sticky nature of the material. In addition, one of skill in the art would expect that purification attempts might result in loss or decrease of the adhesive nature of the material, due to one or more of the following:

1) Bioadhesives are generally polysaccharides, glycoproteins, proteoglycans or lipopolysaccharides. Therefore, they would be expected to be subject to degradation during isolation by, for example, proteases, glycosidases, and/or lipases.

2) Some bioadhesives are known to have chemically reactive groups which may undergo undesirable modification during purification if precautions are not taken. A specific example of this is the mussel adhesive isolated by Waite (U.S. Pat. No. 4,496,397), in which there are numerous o-diphenyl groups which can undergo autooxidation, with resultant loss of adhesive activity.

3) Some known bioadhesives are multicomponent in nature. Thus purification of any one part would result in less than optimal adhesive properties of the isolated material when compared with the natural, multicomponent material. For example, the mussel adhesive noted above contains ". . . a polyphenolic substance that is mixed by the animal's foot with a curing enzyme (phenoloxidase) and a mucosubstance to provide a complex three-component natural adhesive system". In addition, the interconnective tissue of animal cells often involves supramolecular complexes of various proteoglycans (Rollins, B. J., et al., "Fibronectin-proteoglycan Binding as the Molecular Basis for Fibroblast Adhesion to Extracellular Matrices". In *The Glycoconjugates*, Academic Press (1982)).

4) Any dispersion and reformation of a (non-covalently linked) supramolecular complex with adhesive properties runs the risk of incorporating (trapping) material that originally was not part of the adhesive structure. Any decrease in the interconnecting bonds of an adhesive would decrease the adhesive strength of the material. Moreover, contaminants may bind to the adhesive portion of the structure, thereby reducing the adhesive ability of the structure.

5) Many instances of bioadhesion are thought to rely solely upon the forces of capillarity. In these instances the viscosity of the fluid that occupies the capillary spaces will play an important and direct role in the strength of these capillary forces: the higher the viscosity the greater strength of the adhesion. Based upon these facts, it is reasonable to believe that a reduction or elimination of capillary fluid viscosity, during the course of isolation of the adhesive material as would occur upon such treatments as would cause dispersion of a mucilage, would correspondingly reduce or eliminate the adhesive properties of that fluid.

Among fungi which must adhere in aqueous environments, marine fungi adhere to underwater surfaces via mucilages and appendages (Rees, G. and Jones, E. B. G., *Botanica Marina* 27:145, 1984), human fungal pathogens adhere to the cell surfaces of the invaded areas via extracellular polysaccharides (McCourty, J. and Douglas, L. J., *J. Gen. Microbiol.*, 131:495, 1984), and fungal plant pathogens adhere to wet plant surfaces via mucilages (Hamer, J. E., et al., *Science* 239:288, 1988). Despite these observations of fungal adhesion, only rarely has the origin of the adhesion been experimentally demonstrated (Rees, supra). Even less is known about the biochemical nature of fungal mucilages (Ramadoss, C. S., et al., *J. Ag. and Food Chem.*, 33:728, 1985). Although the adhesive nature of fungal mucilages has been postulated, in no case has a fungal mucilage been isolated from the organism, purified, characterized and demonstrated to retain useful adhesive properties. No attempts have been reported, presumably due to the general expectation of difficulties disclosed above.

The fungus *Magnaporthe grisea* is found worldwide as a pathogen of many grasses, where it attacks the aerial parts of the plant. Common synonyms for *M. grisea* include *Pyricularia grisea* and *Pyricularia oryzae*. The fungus can easily be isolated in pure culture form from lesions on infected plants. Asexual spores (conidia) are dispersed to plant surfaces by wind or rain. During warm, humid conditions, these conidia germinate and infect the plant. To infect the plant, however, the conidia must attach to the plant surface. For *Magnaporthe grisea*, this attachment occurs at the conidial tip. Flow chamber studies have shown that conidia adhere tightly by their tips, and that concanavalin A blocks conidial attachment. It has been hypothesized that mucilage might be the agent of attachment (Hamer, supra).

The term mucilage has a generic meaning, and includes many compositions which are, by definition, sticky. The common mucilage used for gluing paper, for example, is comprised of complex plant polysaccharides. This is very different from the polyphenolic mucilage protein obtained from mussel (U.S. Pat. No. 4,496,397), which was identified as a polyphenolic protein rich in 3,4-dihydroxyphenylalanine (dopa) and hydroxyproline. This protein was disclosed as being very difficult to isolate, and the actual bioadhesive is a complex of three distinct components. In particular, it is noted that U.S. Pat. No. 4,496,397 is directed to a process for purifying and stabilizing the catechol-containing polyphenolic protein portion of the bioadhesive, which, as noted above, involves procedures outside of the usual and expected means usually used to isolate and purify "normal" nonmucilagenous proteins.

It is also interesting to note that yeasts which stick to plants have been shown to produce novel extracellular lipids, including a glucose-containing disaccharide linked to lipid. This has been shown to be a glucose disaccharide in which a terminal glucose is beta-linked to the 2-position of another glucose residue. This disaccharide is glycosidically linked to 13-hydroxydocosanoic acid. These yeast lipids have not been shown to be involved in adhesion. See "Extracellular Lipids of Yeasts" (Stodola et al., *Bacteriological Reviews*, Sept. 1967, p. 194–213).

Research on the biochemical nature of the fungal adhesives is particularly difficult due to extremely small amounts of mucilage present in each spore tip, the contamination of extracellular polysaccharides which are secreted when the fungal mycelia are grown in culture and the physical characteristics of the adhesive itself. In particular, it is to be noted that mucilages in natural form, especially in concentrated form, are viscous, sticky substances which adhere to even hydrophobic surfaces, making manipulation and transfer of the substance difficult and losses high at each step. Thus, in view of the particular problems expected to be encountered with fungal spore tip mucilage as well as the general problems encountered with other bioadhesives, it can be understood that isolation and purification of spore tip mucilage in useful quantities was assumed to be difficult and unrewarding, especially in view of the very significant possibility that the material which would be obtained would not retain its adhesive properties. In fact, the inventors of the instant invention made many unsuccessful attempts to purify fungal mucilage prior to the development of the instant invention. In particular, numerous forms of column chromatography were attempted, but great difficulty was encountered in removing the material from the column matrices.

SUMMARY OF THE INVENTION

One aspect of this invention comprises spore tip mucilage isolated from the conidia of *Magnaporthe grisea* having adhesive properties under wet conditions. In a preferred embodiment, the mucilage is further isolated free of conidial cellular material, extracellular mycelial polysaccharides and low molecular weight contaminants.

Another aspect of this invention comprises spore tip mucilage from the conidia of the fungi *Magnaporthe grisea* which has been isolated in a process comprising: (i) growing the fungus in synchronous culture to a growth stage wherein said fungi have produced conidia having mucilage at the tips of said conidia; (ii) harvesting said conidia from said fungi cultures into a solution; (iii) dispersing the mucilage from said conidia by means of gentle disruption of the solution; and (iv) separating conidial debris from the solution to yield purified spore tip mucilage.

DETAILED DESCRIPTION OF THE INVENTION

The isolated mucilage material of this invention provides a bioadhesive with useful properties. The adhesion is nonspecific, thus allowing adhesion to many different surface types without the need for a specific receptor on the surface. The material binds to, and can bind other materials to, very hydrophobic surfaces including polytetrafluoroethylenes (e.g., Teflon ®). The material can be used as a glue underwater immediately after application. A period of drying, typical of many adhesives, is not necessary for the spore tip mucilage. In fact, glued particles can resist high shear forces from the flow of water. These properties provide unique advantages for use in applications in aqueous environments.

The fungal mucilage material is further distinguished from mucilage in its natural form by its isolation in quantities and in a form which allows it to be used conveniently for adhesion of surfaces other than spores to a second surface. Thus, in particular, the following relevant differences are noted:

1) Purified spore tip mucilage is aseptic in the sense that viable conidia have been removed. This is an important feature, particularly for any application where contaminating organisms must be avoided, e.g., medical uses. This is also a consideration from the standpoint that the fungus, upon the germination and growth of contaminating conidia, may then cause an alteration of the adhesive properties of the spore tip mucilage after it has been applied.

2) For purposes of "gluing" or adhering two surfaces together in an efficient manner, it is necessary to eliminate any contaminating third surface, e.g., the conidia, from the adhesive, so as to maximize contact between the two surfaces of specific interest. This is particularly important in applications where the quantities of adhesive and areas of surfaces to be glued are very small.

3) By removing conidia from the mucilage, the mucilage will be of reduced antigenicity, which is again an important consideration for situations where it is to be applied within a living organism.

4) By purifying the mucilage and removing "natural" components that are not necessary for adhesion, the adhesive properties of the mucilage can be quantified so that it may be applied in quantities that are directly relevant to its adhesive activity.

5) During storage at low temperature and subsequent thawing of unpurified mucilage, enzymes or other factors may be released from conidia which alter the adhesive properties of the mucilage or be undesirable in any application in a living organism, particularly a human.

The term "having adhesive properties" means that the adhesive properties of the mucilage when isolated from its natural condition are substantially of the same nature, e.g., strength, versatility, wet efficacy, etc., as in the natural state. This term refers to adhesive properties sufficient, for example, for the industrial uses mentioned herein.

Suitable organisms which can be used as the source of the mucilage include species from the genus Magnaporthe, preferably strains of *Magnaporthe grisea*. Applicants have identified the presence of the spore tip mucilage of the invention in a variety of strains of *Magnaporthe grisea* which have been collected in natural state from locations worldwide. Applicants further believe that other fungi, especially pathogenic fungi which produce similar conidial spores with adherent properties, also produce such mucilage. Likely genera include, for example, Nectria, e.g., *Nectria haematococca* (Jones, M. J. and L. Epstein, *Physiolog. and Molec. Plant Pathol.* 35:453–461 (1989)); Phytophthora, e.g., *Phytophthora cinnamomi* (Gubler, F., A. R. Hardham, and J. Duniec, *Protoplasma* 149:24–30 (1989)); Smittium, e.g., *Smittium culisetae* (Horn, B. W., *Mucologia* 81:742–753 (1989)); Amphoromorpha, e.g., Amphoromorpha entomophila (Blackwell, M. and D. Malloch, *Mycologia* 81:735–741 (1989)); as well as other strains: see, for example, those discussed in the review article by Nicholson, R. L. and L. Epstein in "The Fungal Spore and Disease Initiation in Plants and Animals", G. T. Cole and H. C. Hoch, ed., Plenum Press. Especially preferred plant pathogenic fungi include those which are infective in wet environments. Fungi can easily be isolated in pure culture form, for example, from lesions on diseased plants.

Conventional culturing techniques may be employed for preparing conidia for extraction of the mucilage. However, it has been found that the production of synchronous fungal cultures provide the best yields. This is because the production of this spore tip mucilage is developmentally regulated: initially the mucilage is compact and confined to a special organelle in the top of the spore, but during maturation of the conidium, the compartmentalized mucilage is extruded from the tip to form an expanded mass adhering to the tip. As the conidia age further, the mass diffuses away from the tip and many older conidia (e.g., two weeks or more old) do not display the extruded mass of mucilage. Thus, high yields of material require many conidia at the developmental stage where the mucilage has been extruded but where the mucilage has not yet diffused away from the tip (typically 4-8 days after initiation of culturing), which condition can be provided by, for example, synchronous cultures.

In order to produce the maximum amount of mucilage, therefore, synchronous fungal cultures are preferably produced which contain the majority of conidia at a substantially similar stage of development. Suitable cultural conditions are described in detail below, but are readily adaptable by one of skill in the art.

Synchronous cultures can be produced by preparing a macerated liquid culture of the fungus in suitable culture medium, e.g., complete medium (*Genetics* 114:1111 (1986)). After, for example, two to four cycles of growth and maceration in a blender, the culture typically consists of many small mycelial balls. The cultural requirements for this step are not rigid. Growth in, for example, 2YEG (*Genetics* 122:35 (1989)), complete or minimal media according to the method of Crawford et al., *Genetics,* 114:1111 (1986), at 24°-30° C. for 3-7 days results in the production of usable mycelia. These mycelia can then be spread on agar plates in a nutrient agar overlay, using sterile techniques, and the cultures grown at 20°-30° C., preferably 25° C., under continuous light conditions, preferably about 8000 lux.

When the conidia are at an appropriate stage of development, e.g., when the production of mucilage at the tip of the conidia is maximal, e.g., after 5-7 days of growth under the above-specified conditions, the conidia can be harvested into a solution, for example, water. The bulk of the extracellular polysaccharide contaminant typical of fungal mycelial growth is then washed off. The washing steps comprise several cycles of centrifugation at speeds suitable for pelleting the conidia, followed by resuspending the conidia in water. If the subsequent steps are performed without this initial washing step, the mycelial polysaccharide can account for greater than 95% of the material obtained.

The mucilage is then gently dispersed, e.g., by physical disruption of the conidia suspension which can be provided, for example, by sonication. Preferably, disruption occurs in a solution of detergent, preferably a detergent having a high critical micelle concentration (e.g., $>1$ mM), for example, octylthioglucoside, in order to disperse the mucilage with a minimal contamination of intracellular material from the conidia. Other suitable detergents include, e.g., octylglucoside. When octylthioglucoside, which has a critical micelle concentration of 9 mM, is used, a suitable concentration for dispersing the mucilage is 15 mM.

The disruption step is preferably performed under conditions which result in the production of substantially intact conidia while at the same time dispersing the mucilage from the conidia. The disruption can be performed preferably by sonication, and preferably under conditions sufficiently gentle so as to not solubilize substantial amounts of conidial cellular material, other than the fungal mucilage. These conditions can be determined for any given volume and sonicator by, for example, monitoring the dispersion of the mucilage microscopically. Suitable sonication conditions are those roughly equivalent to a setting of 40 on a VibraCell apparatus (Sonics and Materials, Danbury, Conn.). One convenient means of microscopically monitoring this dispersion is to stain the sonicated conidia, for example, for Magnaporthe, the staining can be effected with the lectin concanavalin A, which binds to the spore tip mucilage at the terminal mannose residues, wherein the concanavalin A is labeled with, for example, a fluorophore, such as, for example, fluorescein isothiocyanate (FITC) (e.g., 100 μg/ml final concentration), and observing the stained conidia via epifluorescence microscopy. If the dispersion has been successful, the extruded mass of mucilage, which normally appears green when observed using epifluorescence microscopy after staining with FITC-ConA while still connected to the conidium, will not be visible as evidenced by a lack of labeling by the FITC-conjugate. Conidial integrity can be observed microscopically at the same time under visible light conditions.

Conidial debris can then be removed; for example, the suspension of conidia and dispersed mucilage can be subjected to low-speed centrifugation, pelleted and filtered to remove debris. Centrifugation can be performed under conditions which are sufficient to pellet substantially all of the insoluble cellular debris without concomitantly pelleting the mucilage.

To yield a solution of highly purified spore tip mucilage, the solution can then be subjected to repeated ultrafiltrations to remove detergent and low molecular weight material, and to optionally concentrate the mucilage. The ultrafiltrations are performed after dilution of the mucilage/detergent mixture with water at a concentration below that of the critical micelle concentration of the detergent. In the case of octylthioglucoside, this requires an about three-fold dilution. Ultrafiltration filters suitable for this purpose have a molecular weight cut-off of, for example, 10,000 daltons. Preferably a series of 5-10 fold dilutions and concentrations can be performed by ultrafiltration using standard techniques. This step removes a large amount of low-molecular weight material with a UV absorbance typical of phenolics. Clumping of mucilage during this step can be ameliorated by repeated pipetting with a micropipette.

Alternatively, the mucilage can be prepared without detergents by sonication of the harvested and washed conidia, followed by centrifugation at, for example, 120,000 $\times g$ for 2 hours (generally $>100,000 \times g$ for $>30$ min.), followed by filtration, e.g., through a 0.8 μm filter, and then a further sonication and filtration through a smaller pore filter to remove conidial debris. This technique takes advantage of the insolubility of the mucilage in water. Ultrafiltration is performed as above, except that it is for the purpose of removing low molecular weight material other than detergent. Other variants of this process can naturally be developed depending on the details involved.

These preparation steps result in an isolated adhesive fungal mucilage which is free from detergent and low molecular weight contaminants, as well as from most high molecular weight material from the conidia. The mucilage can be stored in solutions and can be frozen, for example, at $-20°$ C. It is also possible to lyophilize the mucilage and store it in a dried form, including at temperatures above $-20°$ C., for example, at room temperature, and convert it back to its useful form by the addition of, for example, water.

One mucilage isolated by this invention from *Magnaporthe grisea* was analyzed by a number of standard techniques. Amino acid analysis revealed that it has a composition rich in hydrophobic and hydroxylated amino acids. Thus, alanine, glycine, leucine, threonine and valine each occur at levels greater than 10% by weight of the amino acids present. Arginine, histidine, methionine and tyrosine occur at levels of less than 1%. No unusual secondary amino acids were detected.

Carbohydrate analysis was performed using standard techniques, including composition and linkage analysis. It revealed that mannose is the only sugar present; specifically, mannose disaccharides in which a terminal mannose residue is alpha-linked to the 2-position of another mannose residue. This surprisingly simple carbohydrate component of the biological material contrasts with an initial expectation of finding the typical complex mannan component of fungal cell wall glycoproteins, which contains 6-linked-, 2-linked-, 3-linked- and 2,6-linked-mannosyl residues. The absence of glucose and N-acetyl-glucosamine from the sample demonstrates the absence of glucans and chitin, two other major cell wall carbohydrates found in ascomycetous fungi like *Magnaporthe grisea.* Interestingly, this unique carbohydrate found in the biological material is similar to the 2-linked-disaccharide components of extracellular glycolipids produced by yeasts found sticking to plant surfaces. Stodola, F. H., M. H. Deinema and J. F. T. Spencer, 1967 Extracellular Lipids of Yeasts, Bacteriological Reviews 31:194–213.

NMR analysis performed using standard techniques, preferably in deuterated DMSO rather than $D_2O$, suggests the presence of methoxyl and acetyl protons, the source of which are unknown, as well as long chain aliphatic protons, which may indicate the presence of a lipid component. Taken together, these data provide a discriminating biochemical fingerprint of this composition.

The isolated spore tip mucilages of this invention are remarkable adhesives, capable of adhering surfaces under wet conditions, including both hydrophilic surfaces and hydrophobic surfaces such as Teflon®. For example, latex beads glued to plastic, glass and Teflon® surfaces using the mucilage of Example 3, could not be dislodged under conditions of very high shear force.

The mucilages thus have very wide ranging applications suitable for a wide variety of adhesive needs for gluing essentially any two surfaces together, but especially those requiring adhesion under aqueous conditions. In addition to their use as adhesives, the mucilages of this invention can be used as sealants against water or water-based mixtures (e.g., blood). Adhesion is essentially immediate and can be achieved using a very thin application of adhesive. Procedures are fully conventional and well known to skilled workers.

In particular, the mucilage of this invention can be used for many requirements involving medical and dental procedures where aqueous adhesion or occlusion would enable attachment and repair of body parts which cannot be attached or repaired without either first drying the surfaces, which is in most cases not practical or possible, or which currently require other means of attachment such as sutures or metal pins, especially in microsurgical procedures where the temporary adhesion provided by a bioadhesive such as, for example, spore tip mucilage, could eliminate the need for physical suturing, or for applications which are currently unsolved, such as in the case of bone fragments which are allowed to remain unattached in the hope that they will spontaneously rejoin with the bone from which they came. It is particularly noted that the bioadhesive of this invention is likely to be far less toxic and far more innocuous than many conventional glues which contain solvents or other objectionable materials, for applications involving living material.

Applications other than for medical and dental repairs are also fully included in the present invention. For example, repairs can be made to the hulls of boats while they are still in the water, thus avoiding the need for drydocking in order to effect such repairs, and allowing for repairs to be made at sea. Containers for aqueous fluids could also be glued, even while the surface of the container is wet.

Of course, it is evident that even though the mucilages of this invention have a particular utility for the adhesion under aqueous conditions, the invention is not limited to such applications. Thus, the mucilages can be used for any application requiring the adhesion of two or more surfaces for which the adhesion strength is sufficient, which can be routinely determined by one of skill in the art. These include the gluing of, for example, metal, glass, plastic, wood, paper, leather, painted surfaces and other materials which are capable of being adhesively attached, and especially those which require continued adhesion under aqueous conditions.

In the foregoing and in the following examples, all temperatures are set forth in degrees Celsius and unless otherwise indicated, all parts and percentages are by weight. The abbreviation "STM" is used to denote spore tip mucilage.

The entire disclosures of all applications, patents and publications cited above and below are hereby incorporated by reference.

EXAMPLES

Example 1

Isolation of Spore Tip Mucilage from *Magnaporthe grisea* the fungus strain *Magnaporthe grisea* 4091-5-8 was deposited on Feb. 7, 1992 with American Type Culture Collection (ATCC), 12301 Parklawn Drive, Rockville, Md., 20852, U.S.A., with assigned ATCC No. 74134. The deposit was made pursuant to a contract between ATCC and the assignee of this patent application, E. I. du Pont de Nemours and Company, Wilmington, Del., according to the terms of the Budapest Treaty as set forth in 35 U.S.C. 122 and 37 C.F.R. 1.14.

The above-identified fungus *Magnaporthe grisea,* strain 4091-5-8, was grown as a mycelial culture on oatmeal agar medium for two weeks at 25° C. (Strain 4091-5-8 and oatmeal agar are described by Crawford et al. 1986 *Genetics* 114:1111). About 50 cm² of mycelium from the oatmeal agar was macerated in a blender for 20 seconds in 50 ml complete medium (Complete medium is described by Crawford et al. 1986 *Genetics* 114:1111). The resulting macerated mycelium was transferred to about 150 ml of complete medium and grown with rotary shaking (120 rpm) at room temperature for three days. The three day-old liquid culture was again macerated in a blender for 20 seconds and about 200 additional ml of complete medium was added and the culture grown as above. After two more days the maceration procedure was repeated and medium added such that the final volume of the medium was 750–800 ml. Seven days after the initial inoculation the liquid mycelial culture was used to prepare synchronous cultures of conidia as follows. About 6 ml of mycelium was mixed with about 25 ml of cooled (50° C.), molten 2YEG medium (described by Crawford et al. 1986 *Genetics* 114:1111) containing 1.4% agarose and spread on the surface of 150 mm diameter petri dish containing about 90 ml of solidified water agar (1.4% agar). One hundred twenty plates were prepared in this manner and were incubated at 25° C. under continuous fluorescent lighting (8000 lux). After 6 days the fungal mycelium had grown throughout the top layer of 2YEG agarose and produced many conidia. The conidia were harvested from each plate by adding about 10 ml of water to the plates and rubbing the surface containing the fungal growth with a bent glass rod. The harvested conidia ($8 \times 10^9$) were centrifuged at 4000 $\times$g for 5 minutes. The supernatant was discarded and the pellet of conidia was gently resuspended in 1 liter of water containing 0.05% Tween 20 and 0.1 M NaCl. The centrifugation was repeated as above and the supernatant was again discarded. The pellet of conidia was then resuspended in 50 ml of water containing 15 mM octylthioglucoside and 0.15 M NaCl. Ten ml aliquots were placed in $17 \times 100$ mm polypropylene tubes and then sonicated for about 20 seconds at output setting 45 with a Vibra Cell sonicator (Sonics and Materials, Inc., Danbury, Conn.). The sonicated conidial suspensions were centrifuged at 16,000 $\times$g for 10 minutes. The supernatant was filtered successively through nylon filters with pore sizes of 13 μm (Nitex®, Tetko, Inc., Elmsford, N.Y.), 5 μm (Magna Nylon 66, Microsep, Inc., Honeoye Falls, N.Y.), and 1.2 μm (Magna Nylon 66, Microsep, Inc., Honeoye Falls, N.Y.).

Example 2

Isolation of Spore Tip Mucilage

The procedure described in Example 1 was repeated to produce 100 synchronous cultures. These cultures produced $5 \times 10^9$ conidia that were processed for spore tip mucilage as described in Example 1. The filtrates from Example 1 and Example 2 (i.e., the filtrates from the successive filtering through the nylon filters with pore sizes of 13 μm, 5 μm, and 1.2 μm) were pooled and further processed as described in Example 3.

Example 3

Concentration of Spore Tip Mucilage

The filtrate resulting from the pooled material in Example 2 (100 ml) was then concentrated and washed free of low molecular weight material by repeated concentration and dilution with water using a 350 ml ultrafiltration apparatus with a 10,000 MW filter (Amicon Diaflo®, W. R. Grace & Co., Danvers, Mass.). This procedure effectively removed the material of less than 10,000 MW and allowed a final concentration of the material greater than 10,000 MW. The purification factor for removal of filterable material (i.e., less than 10,000 MW) was approximately 3200-fold. The unfilterable material (i.e., greater than 10,000 MW) was concentrated to 28 ml. This 28 ml was further concentrated to 1 ml using 2 ml ultrafiltration units with a 10,000 MW cutoff (Amicon Centricon®, W. R. Grace & Co., Danvers, Mass.).

Example 4

Characterization of Isolated Spore Tip Mucilage

Carbohydrate and Protein Estimates

Carbohydrate in isolated STM samples was estimated using the phenol/sulfuric acid method described by Dubois et al., *Anal. Chem.* 28:350 (1956). Glucose was used as a standard. The carbohydrate content was estimated to be 2.7 mg in the sample from Example 3. Protein was estimated using the Bradford-Comassie Blue binding assay described by Bradford, M., *Anal. Biochem.* 72:248 (1976). The protein content was estimated to be 860 μg in the sample in Example 3. It is noted that these ratios are based on assays which can be susceptible to interference from the sample.

Gel Filtration Chromatography

The isolated spore tip mucilage from Example 3 was subjected to gel filtration chromatography on a Hewlett Packard 1090 Liquid Chromatograph with a Du Pont Zorbax G-450 column. The running buffer was 100 mM Tris, pH 7.5, 0.1% sodium dodecyl sulfate, 100 mM NaCl. The column was used at a flow rate of 1 ml/minute. Under these conditions the column pressure was about 30 bar. Concentrated spore tip mucilage preparation from Example 3 (50 μl) was applied to the column in a total of 200 μl of running buffer. A chromatogram of this eluate showed The initial material is eluted at greater than 300,000 MW. The largest peak, containing most of the material absorbing at 280 nm, eluted at approximately 14,000 MW.

Carbohydrate Analysis

Three hundred microliters of the sample prepared in Example 3 were analyzed. Alditol acetate derivatization (described in Albersheim et al., i Carbohydr. Res. 5:340 (1967)) and trimethylsilyl (TMS) methy glycoside preparation (described in Chambers et al., *Biochem. J.* 25:1009 (1971)) and exhaustive methylation (described in Hakormori et al., *Biochem. J.* 55:205 (1964)) were performed according to established procedures. The alditol acetate derivatives and the partially methylated alditol acetate derivatives were analyzed on a Hewlett-Packard 5890 gas chromatograph equipped with a Hewlett-Packard mass spectrometer and a 30 meter fused silica SP2330 column. The TMS methyl glycosides were analyzed with a Hewlett-Packard 5890 gas chromatograph equipped with a 30 meter fused silica DB1 column. Glycosyl composition analysis was performed by two methods: 1) analysis of alditol acetate derivatives and 2) analysis of TMS methyl glycosides. Linkage analysis was performed by gas chromatography/mass spectrometry of partially methylated alditol acetate derivatives. Both the alditol acetate analysis and the TMS methyl glycoside showed that the only glycosyl component is mannose and that this component accounts for about 25% of the sample mass. The methylation analysis resulted in two partially methylated alditol acetates: 1,5-di-O-acetyl-2,3,4,6-tetra-O-methyl mannitol and 1,2,5-tri-O-acetyl-3,4,6-tri-O-methyl mannitol. These components originate from terminal and 2-linked mannose residues respectively and are present in a 1:1 ratio. These results indicate that the only significant carbohydrate species in spore tip mucilage is a mannose disaccharide in which a terminal mannose residue residue in linked to the 2-position of another mannose residue. Because the 2-linked mannosyl residue was not destroyed by base during the methylation procedure, it is most likely linked, through an alpha-glycosidic bond, to a non-carbohydrate substituent. This stability to treatment with base suggests that the disaccharide is not linked through a glycosidic bond to serine or threonine residues of the protein substituent. Applicants believe that the disaccharide may be linked directly to the lipid component.

Amino Acid Composition

Amino acid composition was performed by hydrolyzing 100 μl of sample from Example 3 by established procedures (described in Hirs et al., *J. Biol. Chem.* 211:941 (1954)). The hydrolyzed sample was then analyzed using a Beckman 6300 Amino Acid Analyzer. The results of the analysis are shown in Table 1. The amino acid composition is greater than 10% for the amino acids alanine, valine, threonine, glycine, and leucine, and less than 1% for tyrosine, methionine, histidine, and arginine. This method does not detect cysteine or tryptophan.

TABLE 1

Amino Acid Composition of Spore Tip Mucilage

| Amino Acid | % Total |
| --- | --- |
| Tyr | 0.3 |
| Met | 0.3 |
| His | 0.6 |
| Arg | 0.6 |
| Phe | 1.9 |
| Lys | 2.0 |
| Ile | 7.0 |
| Asx | 7.1 |
| Pro | 7.5 |
| Glx | 7.5 |
| Ser | 7.7 |
| Ala | 10.3 |
| Val | 11.5 |
| Thr | 11.7 |
| Gly | 11.9 |
| Leu | 12.1 |

Nuclear Magnetic Resonance Spectroscopy

Four hundred microliters of the sample from Example 3 was dissolved in $D_2O$ and freeze dried. This procedure was repeated. The sample was then dissolved in $D_2O$ and analyzed on Bruker AM250 nuclear resonance spectraphotometer. The analysis resulted in a spectrum with rather broad peaks. This was probably due to the turbid and somewhat viscous solution the sample formed in water. The resonances between 4.9 and 5.2 ppm are due to anomeric protons and indicate that the glycosyl residues are alpha-linked. The resonances between 3.5 and 4.1 are due to the ring protons of the glycosyl residues. There are several sharp peaks between 3.5 and 3.75 ppm which may indicate methoxyl protons. The broad peaks at 1.6-2.4 ppm, 1.2-1.3 ppm, and 0.8-1.2 ppm may indicate acetyl protons, aliphatic methylene protons, and aliphatic methyl protons, respectively. These latter signals are indicative of a lipid component to spore tip mucilage.

To confirm that the resonances indicative of a lipid were indeed from a lipid and not due to residual detergent (i.e., the Tween 20 or octylthioglucoside used in Example 3) STM was prepared without the use of detergents. Conidia were produced, harvested and processed as described in Example 1. At those steps in which Tween and NaCl and octylthioglucoside and NaCl were used, water was used instead of these solutions. After sonication, centrifugation and filtration through 13 and 5 μm filters (performed as in Example 1), the filtrate was centrifuged at 120,000 ×g for two hours. A resultant pellet was resuspended in 2 ml water. Approximately 10 μl of the resuspended pellet and the supernatant were dried on a glass microscope slide and stained with FITC-labeled concanvalin A (final concentration was 100 μg/mm. Both the resuspended pellet and the supernatant showed bright fluorescence when observed microscopically, consistent with the material containing STM. The supernatant was then washed free of low molecular weight material as described in Example 3. The resuspended pellet was further diluted to 5 ml with water and then sonicated for one minute at setting 40 on a Vibra Cell sonicator (Sonics and Materials, Inc., Danbury, Conn.). This material was then filtered through a 0.8 μm filter. The filtered material from the pellet was freeze dried and exchanged with $D_2O$. The freeze drying then was repeated. The residue was dissolved in 300 μl of deuterated DMSO and analyzed on a Nicolet NT360 nuclear magnetic spectrometer. The resultant peaks were much sharper in this spectrum with DMSO as the solvent than in the spectrum from the experiment described above where the solvent was water. The peaks from 0.8-2.4 ppm are present in this spectrum as well, confirming that they are part of STM and not due to residual detergent.

Summary of Biochemical Characterization

Spore tip mucilage, isolated as described in Examples 1, 2 and 3, appeared to be a heterogenous biological material. The gel filtration chromatography showed a number peaks of molecular weight ranging from 300,000-14,000 Daltons. The analyses showed the presence of protein, lipid and carbohydrate, specifically a mannose disaccharide in which a terminal mannose residue is alpha-linked to the 2-position of another mannose residue. The NMR peak at 1.2 ppm strongly suggested the presence of lipid as this is the shift expected for aliphatic methylene groups. Further, the NMR also suggested methoxyl and acetyl derivatization in STM. The portion of STM that contains these derivatives is currently unknown. Thus the isolated material was of a complex nature and contained polypeptide, a mannose disaccharide and a lipid component. Despite the complex, heterogenous nature of the isolated material, the procedure described yielded material free of major contaminants as was clearly indicated by carbohydrate analysis. The conidial walls of Ascomycete fungi (*Magnaporthe grisea* belongs to this taxonomic group) contain significant quantities of large mannans and chitin. These represent two likely contaminants in a procedure that utilizes extraconidial material. However, the carbohydrate analysis clearly showed that large mannans and N-acetyl glucosamine, the monomer of chitin, were not present.

Example 5

Adhesion of Latex Beads to Plastic Coverslips Using Intact STM

A plastic coverslip (SPI ®; Supplies, Div. of Structure Probe, Inc., West Chester, PA; cat. no. 1244) was taken directly from its box using forceps and placed onto the surface of a synchronous culture (prepared as in Example 1) of M. grisea, strain 0-42 (described by Crawford et al., *Genetics* 114:1111 (1986)). The coverslip was gently pressed against the surface until the air was eliminated between the coverslip and the fungal culture. The coverslip was then carefully lifted from one edge using a forceps and placed on the bench top so that the side that contacted the culture was facing up. This served as the test coverslip. Several drops of a solution (0.2% solids) of polystyrene latex beads 0.5 $\mu$m diam. (obtained in a dropper bottle from Ladd Research Industries, Inc., Burlington, Vt.) were dropped directly from the bottle onto the coverslip. The drops on the test coverslip assumed a much lower profile than when placed upon an untreated coverslip, indicating a difference in hydrophobicity. The solution of latex beads was then drawn off the coverslip by absorbing the fluid with a Kimwipe tissue which contacted the fluid at just one edge of the fluid pool. A few drops of FITC-ConA (fluorescein-concanavalin A) solution (obtained from Polysciences, Inc., Warrington, Pa.) were then applied and removed in the same manner. (Fluorescein-labelled Concanavalin A, which recognizes alpha-linked mannose or glucose residues, stains STM intensely. This is due to the large number alpha-linked mannose disaccharides in STM). Finally, the test coverslip was mounted in a flow chamber (ca. 50 $\mu$m high $\times$11 mm wide) connected to a FMI lab pump model RP-D (Fluid Metering, Inc., Oyster Bay, N.Y.). As a control coverslip, another coverslip was prepared as above, but, instead of pressing it against the surface of a fungal culture it was pressed against the surface of water agar and then processed as was the test coverslip. Drops of latex solution did not spread over the surface of the control coverslip as they did on the test coverslip. A coverslip surface with adhering latex spheres was observed using differential interference contrast and epi-fluorescence optics on a Zeiss Axiphot light microscope before and after the pump was activated for 2-3 min. Pump effluent, distilled water, was measured to be generated at a rate of about 175 ml/min.

No latex beads or fluorescence were visibly associated with the coverslip which had been pressed against water agar. In contrast, patches (which fluoresced) and sheets (which did not fluoresce as brightly) of latex beads were observed and photographed adhering to the test coverslip. Apparently very thin films of spore tip mucilage (STM), sometimes too thin to fluoresce perceptibly, were enough to glue beads to the coverslip sufficiently to withstand the force of the pumped water. The hydrophobicity of the latex suspension on the control and test coverslips were dramatically different from each other, as judged from the different profiles (contact angles) of the drops. This difference is an indication of the efficiency of STM application to the coverslip using these very simple methods of generating STM and applying it to a surface for use as a glue.

Example 6

Adhesion of Latex Beads to Glass and Teflon Using Intact STM

Experiments similar to those described in Example 5 were conducted using glass or Teflon-PFA fluorocarbon film, obtained from E. I. du Pont de Nemours and Company, Wilmington, Del., instead of plastic coverslips. A dry, No. 1 glass coverslip (VWR Scientific) was taken directly from its box and placed onto the surface of a synchronous culture of M. grisea strain Ken 60-19 (described by Crawford et al., *Genetics* 114:1111 (1986)) in the same manner as described in Example 5. After 2 minutes the coverslip was lifted from the culture surface using forceps and placed on the bench top so that the side that contacted the culture was facing up. A droplet of polystyrene latex bead suspension was then applied to the coverslip in the same manner as described in Example 5. The coverslip was then lifted from the bench and held using forceps under the surface of water in a beaker. The coverslip was then vigorously agitated by swishing the coverslip from side to side under water in a direction perpendicular to the plane of the surface of the coverslip. The coverslip was then lifted from the water and placed onto the surface of a glass microscope slide which also held a drop of FITC-ConA. The coverslip was positioned so that the coverslip surface that had originally contacted the fungal culture and latex suspension was oriented down and thus brought into contact with the drop of FITC-ConA. When Teflon-PFA film was used all of the above procedures were followed except that the film was washed under the stream of water from a fully open tap rather than by swishing in a beaker of water. When examined using a microscope as described for Example 5, beads were seen to adhere to glass and Teflon only in areas that also fluoresced, indicating that the beads had been glued to these surfaces by STM.

Example 7

Adhesion of latex Beads to Teflon Using Isolated STM

A sample of isolated STM (obtained as described in Example 3) was stored in a closed eppendorf tube at $-20°$ C. and thawed to room temperature just prior to use. A 5 cm$\times$5 mm strip of Teflon-PFA film was positioned so that the center of the strip was held in place over the opened mouth of the eppendorf tube. With a finger holding the strip tightly over the mouth of the tube the tube was inverted so that the isolated STM within the tube was brought into contact with that portion of the Teflon strip that covered the mouth of the tube. After repositioning the tube upright, the strip was then placed on the bench so that the side that had contacted the isolated STM was facing up: this served as the test side. A drop of polystyrene latex bead suspension (0.5 $\mu$m diameter, from Ladd Research Industries, Burlington, Vt.) was applied to the test side of the Teflon strip in the same manner as was used in Example 5 to apply a drop of latex suspension to the test coverslip. The strip was then held taut by its ends between two hands, with the test side up, 12 inches below a fully opened water tap directly in the stream of water for 20 seconds. The test side of the strip was then examined using a light microscope in the same manner as described in Example 5. Polystyrene beads were found stuck to the area of the strip that had contacted the isolated STM. Beads were not stuck to other areas of the test side of the strip that had not been exposed to isolated STM.

Isolated STM was also tested for gluing polystyrene latex beads to Teflon-PFA using a flow chamber (as in Example 5) instead of holding the Teflon under a stream of running water. A 2 cm square of Teflon was exposed to isolated STM in the same manner as described for the strip in the previous paragraph. The Teflon square was then placed on the bench with the test side facing up. A drop of a suspension of FITC-tagged, polystyrene latex beads (Polysciences, Warrington, PA) was then dropped onto the test side of the square directly from the dropper bottle in which the suspension had been obtained. Fluorescent beads were used to facilitate the detection of adhering beads. The square was then mounted in and flushed using the flow chamber as described in Example 5. Examination of the square (while still mounted in the flow chamber) using epi-fluorescence light microscopy showed that the test side of the square exposed to isolated STM was coated heavily with latex beads. As a control, a different Teflon square, not exposed to isolated STM, was processed separately. Examination of the control square not exposed to isolated STM showed dramatically fewer beads stuck to its surface.

Example 8

Identification of Spore Tip Mucilage From a Variety of M. Grisea Strains

A variety of M. grisea strains were grown and tested for their ability to produce spore tip mucilage (STM). Strains examined are listed below in Table 2.

TABLE 2

| Strain | Origin | Host |
|---|---|---|
| 4091-5-8 | Laboratory strain | E. curvula; E. coracana; E. indica |
| T5 | Brazil | Triticum aestivum |
| 0-70 | Philippines | O. sativa - rice |
| 0-137 | China | O. sativa - rice |
| 0-142 | China | O. sativa - rice |
| 0-172 | Arkansas, U.S.A. | O. sativa - rice |
| 0-184 | Texas, U.S.A. | O. sativa - rice |
| 0-188 | Texas, U.S.A. | O. sativa - rice |
| 0-190 | Korea | O. sativa - rice |
| 0-219 | Ivory Coast, Africa | O. sativa - rice |
| 0-222 | Guinea, Africa | O. sativa - rice |
| 0-250 | India | O. sativa - rice |
| 0-256 | South Africa | O. sativa - rice |
| 0-281 | Egypt | O. sativa - rice |
| G22 | Japan | E. coracana |
| G40 | Mississippi, U.S.A. | S. secundatum |
| G81 | Georgia, U.S.A. | P. glaucum |
| G123 | Georgia, U.S.A. | P. glaucum |
| G161 | Philippines | P. purpuricum |
| G172 | Uganda, Africa | E. coracana |
| G183 | Delaware, U.S.A. | Digitaria sp. |
| G226 | Gabon, Africa | Zea mays |

In the above Table, the genus Eragrostic curvula is listed as E. curvala; Eleusine coracana as E. coracana; Eleusine indica as E. indica; Oryza sativa as O. sativa; Stenotaphrum secundatum as S. secundatum; Pennisetum glaucum as P. glaucum; and Pennisetum purpuricum as P. purpuricum.

Cultures of the straines listed in Table 2 were grown as mycelia on oatmeal agar medium for one week at room temperature. Oatmeal agar mycelial plating is described by Crawford et al. 1986 Genetics 114:1111. After one week 2 mm plugs of each culture were reinoculated into fresh oatmeal agar and incubated at 25° C. under cool white fluorescent light for one week.

At the end of one week the cultures were observed by low magnification stereo light microscopy for the presence of STM at the tips of the conidia. In an 80×stereo microscope using a combination of reflected and transmitted light, bright droplets were apparent at the tips of the conidia on all cultures.

After another week of incubation, conidia were harvested from each oatmeal agar culture by applying 150 μl droplet of a solution of fluorescein isothiocyanate labeled concanavalin A (FITC-ConA), (final concentration, 200 μg/ml) to the surface of the mycelium and rubbing with a sterile transfer pipet. The conidia were transferred to a glass slide and examined via epifluoresence microscopy. Microscopic observation revealed that the bright droplets originally observed at the tips of the conidia under the 80×stereo microscope were now stained by the FITC-ConA and it was concluded that these droplets were indeed STM.

Fluorescein isothiocyanate labeled concanavalin A (FITC-ConA) labeling of carbohydrates is a technique well known in the art and has been used to identify the presence of terminal alpha-linked mannose residues in a number of carbohydrates. (Hamer et al. 1988 Science 239, 288-290). STM stained with FITC-ConA normally appears as a fluorescent green mass when observed using epifluoresence microscopy. After staining, STM is clearly visible as an amorphous mass at the tip of the conidia. Results of FITC-ConA staining are given in Table 3.

TABLE 3

| STRAIN | LEVEL OF STM |
|---|---|
| 4091-5-8 | + |
| T5 | + |
| 0-70 | − |
| 0-137 | + |
| 0-142 | + |
| 0-172 | + |
| 0-184 | + |
| 0-190 | + |
| 0-219 | + |
| 0-222 | + |
| 0-250 | + |
| 0-256 | + |
| 0-281 | + |
| G22 | + |
| G40 | + |
| G123 | + |
| G172 | + |
| G226 | + |

In the above Table, a plus sign (+) indicates that hundreds of spores were observed showing STM. A minus sign (−) indicates that hundreds of spores were observed, none of them showing STM.

As the data in Table 3 indicates, all but one of the strains examined, (0-70), contained some level of STM at the tips of the conidia. The percentage of conidia in each strain which exhibited presence of the mucilage varied, depending on culture conditions. It should be noted that even in the (−) strain (0-70), some stained material was observed dispersed in the culture which may indicate the presence of disseminated STM.

This Example clearly demonstrates that the presence of STM at the tips of the conidia is a broad phenomenon spanning many different strains from different hosts and from diverse geographical regions, and is not restricted to a single strain of M. grisea.

We claim:

1. A purified spore tip mucilage isolated from conidia of Magnaporthe grisea which has been isolated free of conidial cellular material, extracellular mycelid polysaccharides and low molecular weight contaminants, wherein said purified mucilage has adhesive properties under wet conditions, and wherein said mucilage has mannose as the sole carbohydrate component wherein said mannose is comprised of disaccharide units having a terminal mannose residue linked to a proximal mannose residue and wherein the terminal mannose residue is attached via an alpha-linkage to the 2-position of the proximal mannose residue.

and further wherein said mucilage has a polypeptide component which is rich in hydrophobic and hydroxylated amino acids, and a lipid component.

2. A spore tip mucilage from the conidia of the fungi *Magnaporthe grisea* which has been isolated in a process comprising:

i. growing the fungi in synchronous culture to a growth stage wherein said fungi have produced conidia having mucilage at the tips of said conidia;

ii. harvesting said conidia from said fungi cultures into a solution;

iii. dispersing the mucilage from said conidia by means of gentle disruption of the solution; and iv. separating conidial debris from the solution to yield purified spore tip mucilage.

3. The mucilage of claim 2 isolated by a process further comprising after step ii:

iia. washing said harvested conidia to remove contaminating mycelial extracellular polysaccharide.

4. The mucilage of claim 3 isolated by a process wherein at step iii said dispersing is performed by sonication in a solution optionally comprising detergent and further wherein said sonication is performed sufficiently gently so as not to solubilize substantial amounts of conidial components other than the mucilage.

5. The mucilage of claim 4 isolated by a process further comprising after step iv:

v. ultrafiltrating said solution one or more times to remove said detergent and low molecular weight contaminants, and, optionally, whereby said ultrafiltrating further concentrates said mucilage to yield a solution of highly purified spore tip mucilage.

* * * * *